United States Patent [19]
Hamilton

[11] Patent Number: 5,391,141
[45] Date of Patent: Feb. 21, 1995

[54] ADJUSTABLE SIZE AND VARIABLE PRESSURE REGULATED MEDICAL BINDER USED BY A PATIENT AFTER HER OR HIS BODY SURGERY

[76] Inventor: Josef N. Hamilton, 1624 S. Forrest, Westport, Wash. 98595

[21] Appl. No.: 974,139
[22] Filed: Nov. 10, 1992
[51] Int. Cl.⁶ .............................................. A61F 5/02
[52] U.S. Cl. ..................................... 601/151; 602/13; 128/846
[58] Field of Search .................... 128/96.1, 118.1, 874, 128/DIG. 20, 846; 602/13; 2/44; 601/148-152

[56] References Cited

U.S. PATENT DOCUMENTS

| | | | |
|---|---|---|---|
| 2,493,406 | 5/1947 | Hicks | 128/118.1 |
| 3,717,145 | 2/1973 | Berndt | 128/DIG. 20 |
| 4,120,297 | 10/1978 | Rabischong | 128/DIG. 20 |
| 4,413,620 | 11/1983 | Tucker | 128/24 R |
| 4,641,642 | 2/1987 | Williams | 128/96.1 |
| 5,062,424 | 11/1991 | Hooker | 128/897 |

Primary Examiner—Michael A. Brown
Assistant Examiner—David J. Kenealy
Attorney, Agent, or Firm—Roy E. Mattern, Jr.

[57] ABSTRACT

After body surgery a patient has at her or his command the ability to create a suitable binding pressure in the locale of her or his body wound. An inflatable cushion, also referred to as an air bladder, is located over and beyond the wound. This positioning of the inflatable cushion is maintained by a strong netting which surrounds the body portion, and passes directly on and over the inflatable cushion. This surrounding netting is comfortably sized by the adjustment of selected spaced fasteners. The air pressure may be increased by the patient, or a person aiding the patient, by hand squeezing sequences of a hand gripping air bulb pump. Or the air pressure may be regulated by the patient, using the controls of equipment, preferably arranged on a self contained upright wheeled cart, having a battery electrical power source, an electric motor, an air compressor, a battery charger, and both an electrical switching control, and a pressurized air pressure reducing valve, arranged together in a control box, which is movable from the upright wheeled cart to a bed position, within the convenient reach of the patient, via the utilization of tethered pressure air line; and electrical circuit wires.

2 Claims, 4 Drawing Sheets

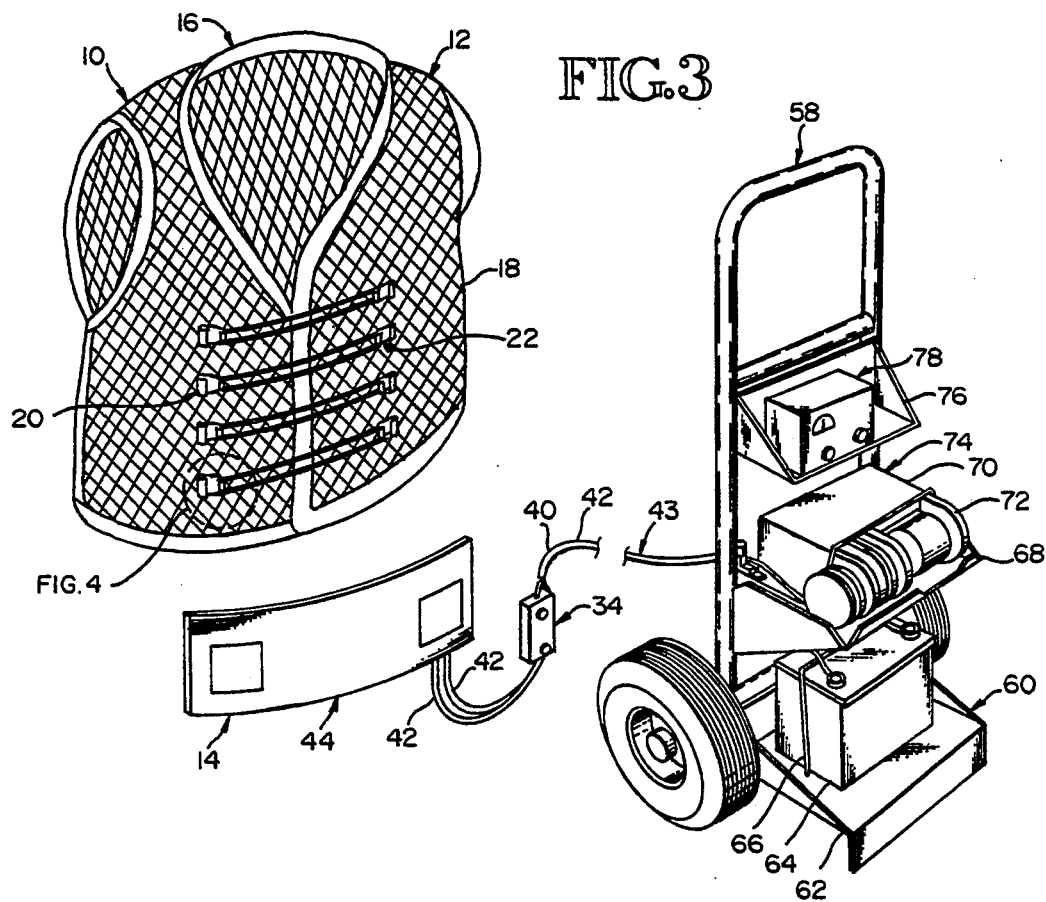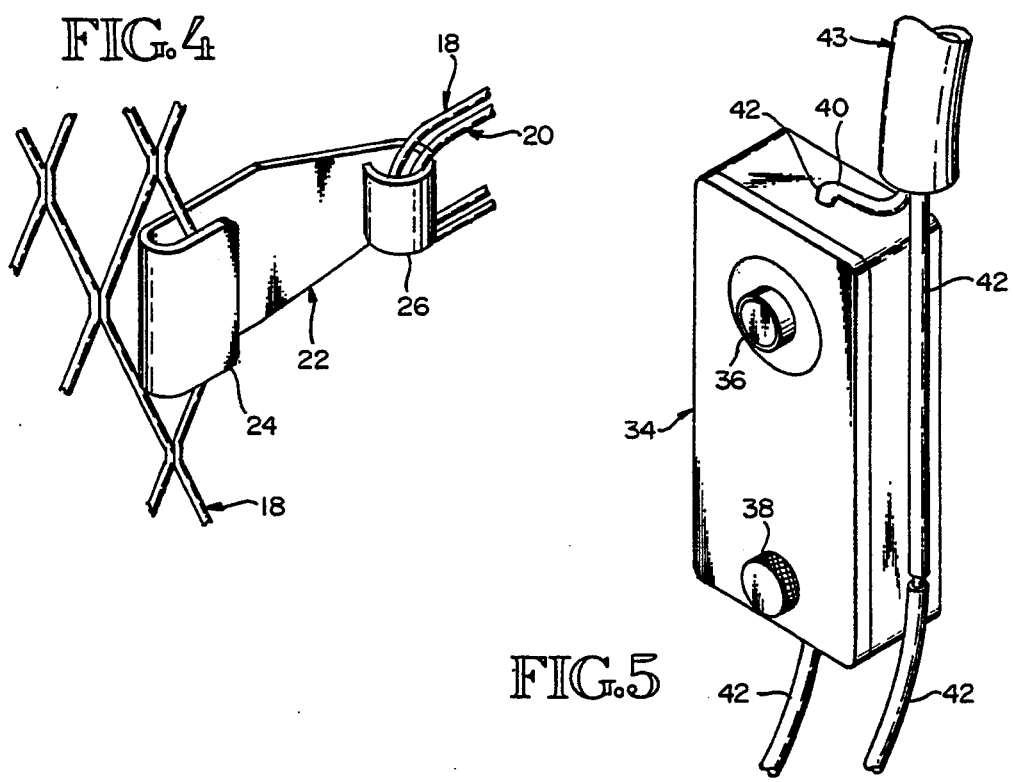

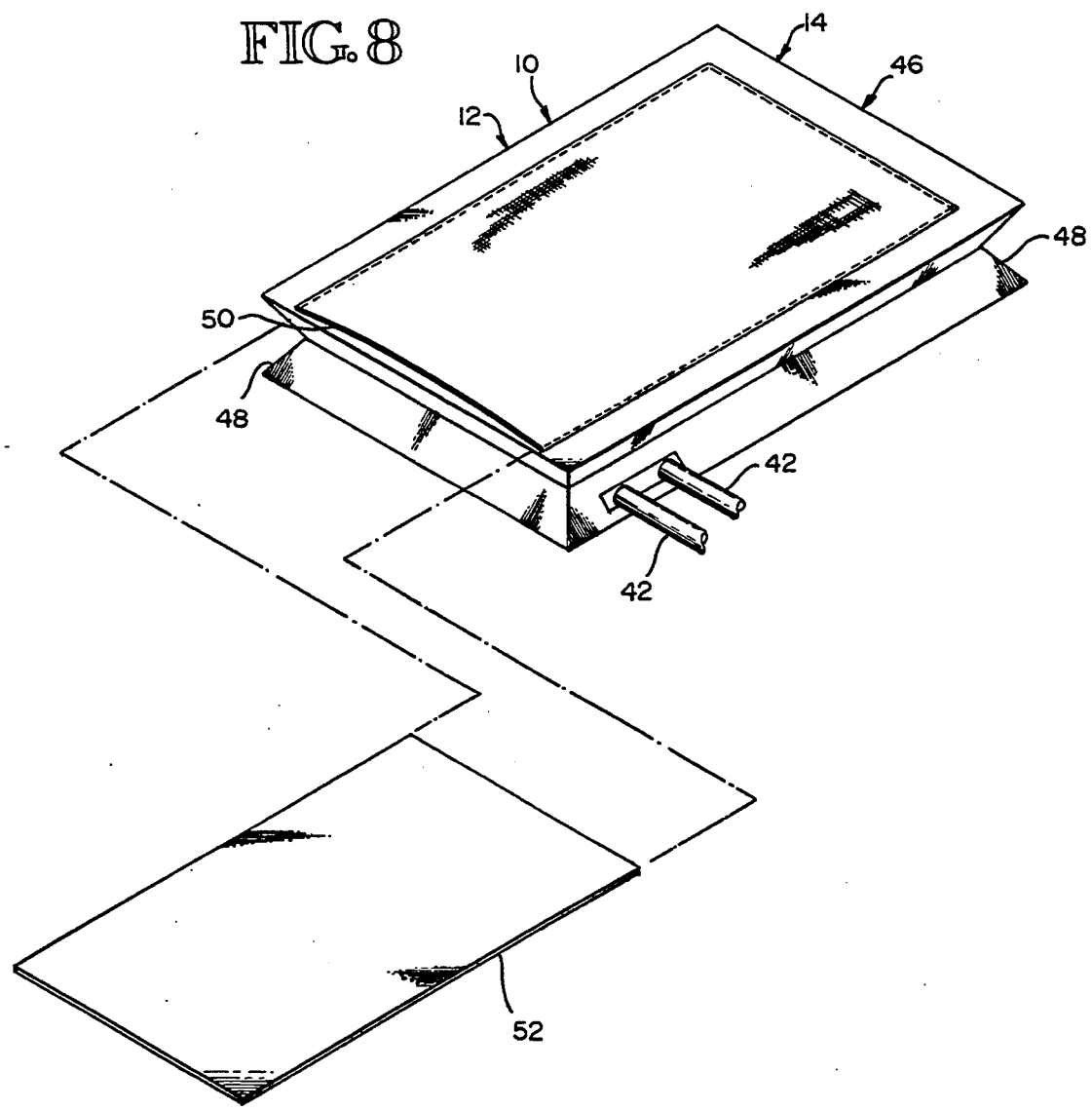

ADJUSTABLE SIZE AND VARIABLE PRESSURE REGULATED MEDICAL BINDER USED BY A PATIENT AFTER HER OR HIS BODY SURGERY

BACKGROUND

During a person's recovery after his or her open heart surgery, and/or his or her abdominal surgery, coughing occurs to expectorate phlegm in clearing his or her lungs. To minimize the pain, he or she holds a conventional pillow against his or her chest to protect the sternum and other body portions, where surgical entries have been undertaken and now are healing, i.e. the wound. Or, preferably, he or she holds a medical pillow, as provided by following the teachings of Herbert Lagin set forth in his U.S. Pat. No. 4,683,601 of 1987. Or, preferably, he or she holds a protective pad for post-operative recovery as provided by following the teachings of Janet L. Yon in her U.S. Pat. No. 4,829,613 of 1989.

When a patient uses these pillows or pads, he or she reduces pain and increases his or her comfort when coughing and moving. Although the benefits realized are noteworthy, greater comfort with less pain is still wanted.

SUMMARY

Especially after a person has undergone open heart surgery, then to reduce the pain he or she experiences when coughing occurs to expectorate phlegm, he or she wears a vest made of strong netting, which in turn positions an inflatable cushion positioned over the healing wound. The combination of the vest, which is well fitted by adjusting portions thereof, and the inflated cushion or bladder, which is selectively inflated to a pressure determined by the patient, serves as an adjustable medical patient binder, providing a patient with more control and comfort, than he or she would be able to obtain by using a conventional pillow, the medical pillow, or the protective pad, as illustrated and described in U.S. Pat. Nos. 4,683,601 and 4,829,613.

Preferably, the inflated bladder or cushion is one which is selected from different embodiments, such as either a smaller one used in taking a person's blood pressure, or a larger one, often having an inflatable chamber with pleated sides and with a top surface pocket to hold a shape determining plate.

Although a hand held and squeezed pump bulb could be used to inflate the selected cushion or bladder, preferably a hand maneuverable cart is provided to position, hold, and store equipment, to be used by a patient, in selecting the inflated pressure of his or her inflated bladder or cushion, which is held in a binding position by the well fitted vest made of strong netting.

The equipment held and stored on the hand cart preferably is a battery electrical power source, a battery charger, an electric motor, an air compressor driven by the electric motor, and both an electrical switching control, and a pressurized air pressure reducing valve, arranged together in a control box, stored on the hand cart, until placed on the patient's bed within his or her convenient reach, by utilizing tethered pressure air lines and electrical circuit wires.

DRAWINGS

Preferred embodiments of the adjustable size and variable pressure regulated medical binder used by a patient after her or his body surgery are illustrated in the drawings, wherein.

Figure 1:
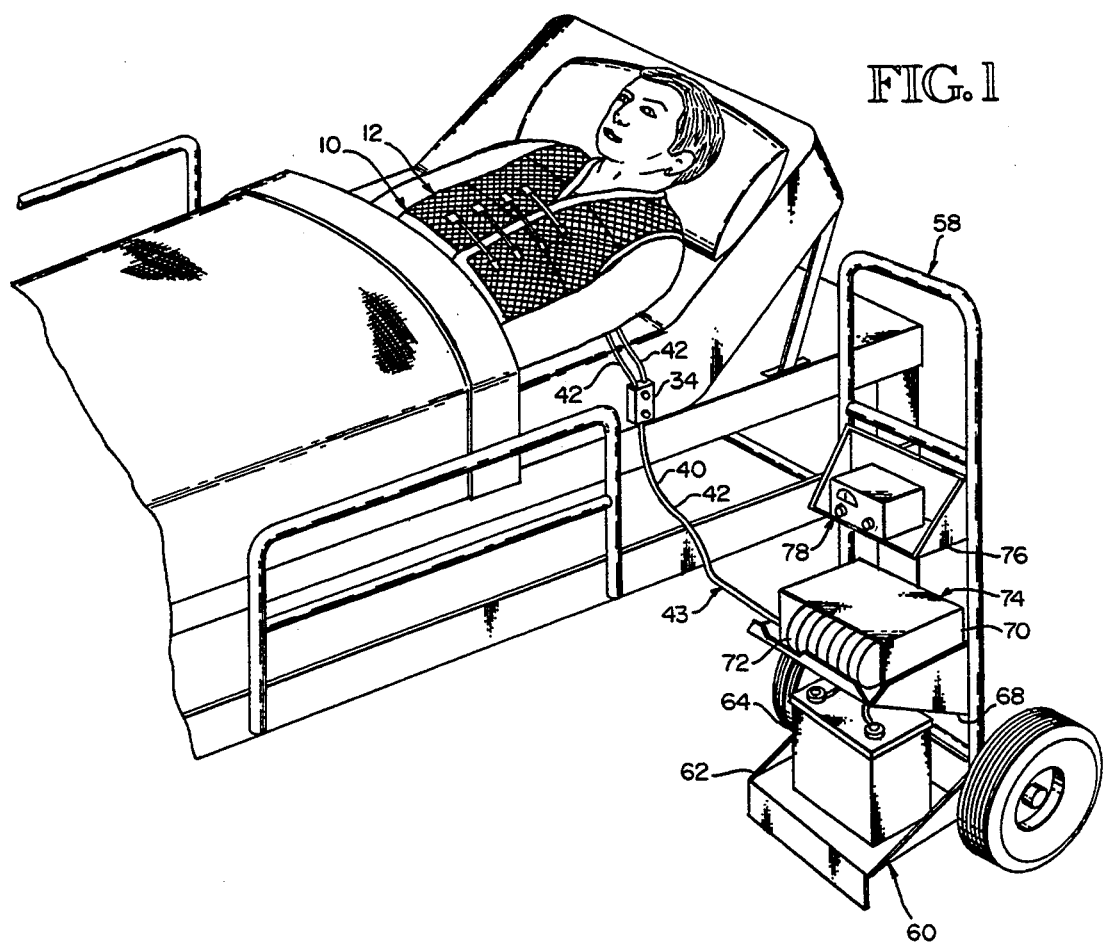
FIG. 1 is a partial perspective view of a patient resting in a hospital bed following open heart surgery, who is wearing the adjustable size and variable pressure regulated medical binder, having controls within his reach to operate equipment arranged on a hand cart.
Figure 2:
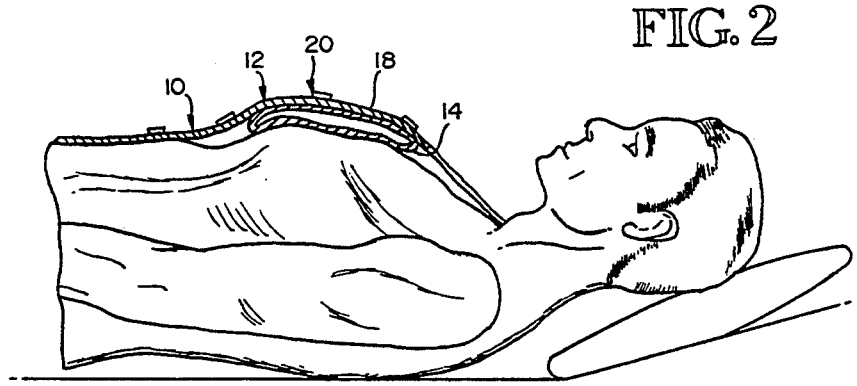
FIG. 2 is a partial side view with portions removed to show the positioning of the inflatable cushion or bladder over the healing wound and beyond, being held in place by the strong netting arranged as a vest, and adjusted in size by spaced fasteners.
Figure 6:
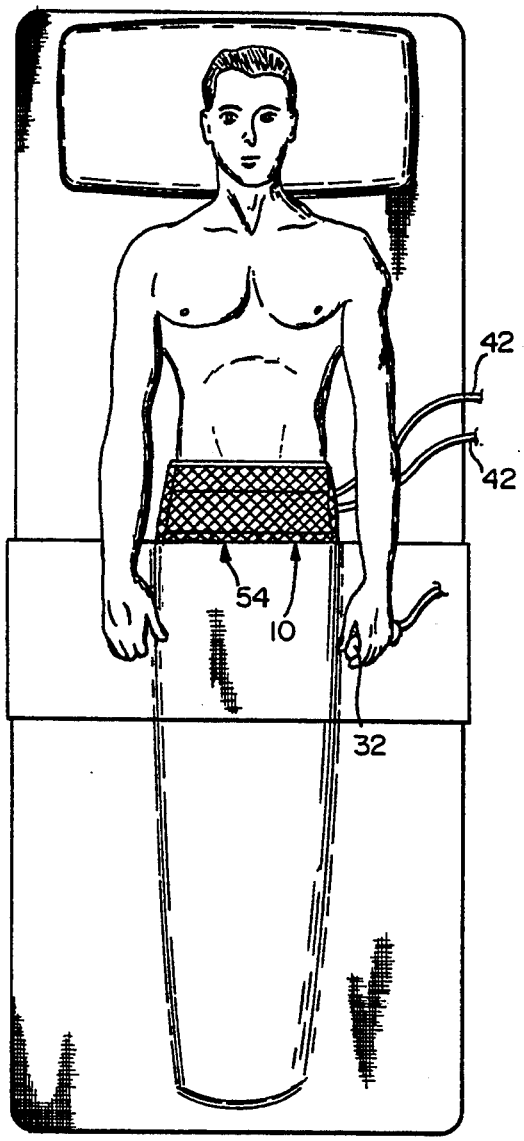
Figure 7:
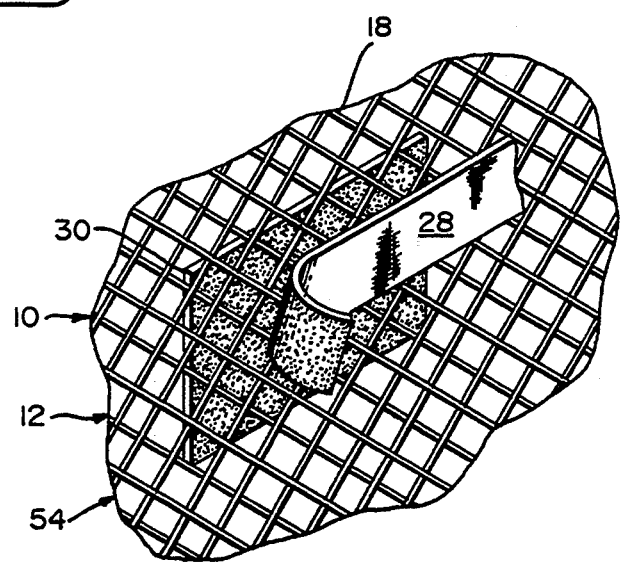

FIG. 3 is a perspective view of all the components before their use, as shown in FIGS. 1 and 2: the strong netting arranged as a vest; the inflatable cushion; the control box with an electrical switching control, and an air pressure reducing valve; the tethered pressure air lines and electrical circuit wires; the hand cart supporting the battery charger, the electric motor, air compressor, and battery;

FIG. 4 is a partial view of portions of the strong netting of the vest, where one end of the cross chest fastener assembly is shown centering on a fastener unit having at one end a large hook to receive a portion or portions of the strong netting, and at the other end a smaller hook to receive one end of a dual continuous loop of cord material, or strong netting material;

FIG. 5 is a perspective view of the control box, illustrated in FIGS. 1 and 3, having an electrical switch at the top to initiate operation of the air compressor, and a compressed air valve at the bottom to release portions of the compressed air from the compressed air cushion or bladder;

FIG. 6 is a top view of another patient resting in a hospital bed following surgery undertaken in lower portions of his body, who is wearing another embodiment of an adjustable size and variable pressure regulated medical binder;

FIG. 7 is a partial perspective view of another fastener assembly utilizing hook and loop fasteners to position, to tighten, and to hold the strong netting of an adjustable size and variable pressure regulated medical binder; and FIG. 8 is an exploded perspective view of an embodiment of a larger inflated cushion or bladder having pleated sides, a top horizontal pocket with a side entry, and a shape determining plate, which is inserted into the pocket, before this larger bladder or cushion is placed over and beyond the patient's surgical wound.

DESCRIPTION OF PREFERRED EMBODIMENTS

In the drawings, preferred embodiments are shown of the adjustable size and variable pressure regulated medical binder 10 used by a patient after her or his body surgery. In FIG. 1, a patient is shown as he is resting following his open heart surgery. He is wearing and using the post open heart surgery embodiment 12 of the adjustable size and variable pressure regulated medical binder 10.

As shown in FIGS. 2 and 3, there is an air cushion 14, also referred to as an air bladder 14, which is placed over the locale of the surgical wound. Then a vest 16 made of strong netting 18 is positioned directly over the air cushion 14 and continued on and around the chest portions of the patient.

The close fitting of the vest 16 is undertaken by using spaced fastener assemblies 20, as shown in FIGS. 1 and 3. The specific fasteners are optionally selected, such as the rectangular bar 22 shown in FIG. 4, which has at the opposite ends thereof, rolled back hook ends 24, 26 to position portions of the strong netting 18. Another selected specific fastener has hook 28 and loop 30 fastener components, as illustrated in FIG. 7.

Upon completion of the fitting of the adjustable size and variable pressure regulated medical binder 10, in respect to the air cushion 14 being located over the locale of the surgical wound and the strong netting 18 being securely fastened by using spaced fastener assemblies 20, then the patient is given the opportunity of gradually increasing the air pressure of the air cushion 14 to a comfortable level to reduce his or her pain and/or to avoid pain.

The air cushion 14 could be inflated to a higher pressure level by the patient using a hand gripping air bulb pump 32, as shown in FIG. 6 . Preferably, however , a control box, supporting an electrical switch 36 and an air valve 38, with respective electrical wires 40, and air conduits 42, which are at places enclosed within a cover 43, is located nearby the patient, as shown in FIGS. 1, 3, and 5, for his or her convenient operation.

The air cushion 14 may be of a smaller size 44, as shown in FIG. 3, or of a larger size 46, as shown in FIG. 8. The larger size 46 has side pleats 48, and a top pocket 50 to receive a slide-in plate 52 which helps to determine the overall rectangular configuration of this larger air cushion 46.

In FIG. 6, a patient is shown in bed recovering from surgery performed on a lower portion of his body. Another embodiment 54 of the adjustable size and variable pressure regulated medical binder 10 is illustrated in this FIG. 6. Again, an air cushion 14 will be placed over the locale of the surgical wound. Thereafter, the strong netting will be snugly arranged over the air cushion 14 and around the body portions of the patient. Thereafter, the patient, by using a hand gripping air bulb pump 32 as shown in FIG. 6, is able to keep the pressure of the air cushion 14 at a level sufficient to reduce his pain level. This embodiment 54, can also be used with the air compressing and pumping means 56 illustrated in FIGS. 1, 3, and 5.

Preferably, for use in hospitals, air compressing and pumping means 56 are provided on a hand cart 58 with shelves 60, as shown in FIGS. 1, 3, and 5, in respect to their storage, transport, and operations. On a lower larger shelf 62, a storage battery 64 is secured by the fastener assembly 66. Preferably the battery 64 utilizes a jelly like electrolyte.

On the middle larger shelf 68 an electric motor 70 and air compressor 72 are arranged as a combination 74. On the top smaller shelf 76 a battery charger 78 is positioned.

The control box 34, with the electrical switch 36 and air valve 38, the electrical wires 40 and the air conduits 42 are all collected together, when not in use, and supported on the hand cart 58.

The strong netting 18, and air cushion 14 before use are disinfected, sanitized, fumigated, and/or cared for to avoid the transmittal of infections, bacteria, and/or diseases. Other portions such as the control box 34 and the adjacent electrical wires and air conduits may also be so cared for to avoid such transmittals.

The battery charger has the battery terminal connectors and leads, and also a power cord and plug for connecting to the hospital or clinic electrical circuit. These battery charger accessories are not illustrated.

By the patient directly utilizing a respective embodiment of these adjustable size and variable pressure regulated medical binders 10, or by other persons so using a selected binder 10 following the requests of a respective patient, a patient is able to reduce his or her pain following surgery, when the locale of the surgical wound might otherwise be strongly stressed during body movements.

I claim:

1. A hand truck supported assembly of intercooperating components, centering on the utilization of an adjustable size and variable pressure regulated medical binder used by a patient after her or his open heart surgery, comprising:

a. a hand truck having a vertical frame, a handle at the top of the frame, axle and wheels at the bottom of the frame, spaced shelves secured to the frame and extending horizontally out from the vertical frame;

b. an adjustable size and variable pressure regulated medical binder supported on the spaced shelves of the hand truck, comprising, in turn:

i. an inflatable air cushion for placement over the locale of the surgical wound during a healing period;

ii. an air compressing and pumping means to inflate the inflatable cushion to a pressure selected by the patient; and iii. a strong netting arranged as a vest and having adjustable fastener assemblies for fitting closely over the inflatable cushion, when the inflatable cushion is over the locale of the surgical wound, and to continue on for fitting closely around a body portion of the patient, to thereby keep the inflatable cushion located over the locale of the surgical wound, when the inflatable air cushion is inflated to pressures selected by a patient, to assist the patient in reducing his or her pain, whenever coughing or other happenings occur, which tend to try to stress the healing wound;

c. wherein, said air compressing and pumping means is an assembly of an electric motor, an air compressor driven by the electrical motor, electrical wires connected between a source of electrical power and the electric motor and between the electric motor and a control box having an electrical switch, air conduits connected between the air compressor, the inflatable air cushion and an air valve in the control box, and control box including both the electrical switch comprising means for starting and stopping the electrical power used in operating the electric motor, and the air valve connected to the air conduits, which comprises means for releasing pressurized air from the air conduits, and the control box is positioned on a shelf of the hand truck, and there are sufficient lengths of electrical wires and air conduits so the control box can be placed within the convenient reach of a patient, when needed.

2. A hand truck supported assembly, as claimed in claim 1, wherein the air compressing and pumping means has: a battery as a source of electrical energy and a battery charger for charging the battery, which are both supported on the shelves of the hand truck.

\* \* \* \* \*